United States Patent
Sijbrandij et al.

(10) Patent No.: US 8,669,525 B2
(45) Date of Patent: Mar. 11, 2014

(54) SAMPLE INSPECTION METHODS, SYSTEMS AND COMPONENTS

(75) Inventors: Sybren Sijbrandij, Wakefield, MA (US); John Notte, IV, Gloucester, MA (US); William B. Thompson, Los Altos, CA (US)

(73) Assignee: Carl Zeiss Microscopy, LLC, Thornwood, NY (US)

( * ) Notice: Subject to any disclaimer, the term of this patent is extended or adjusted under 35 U.S.C. 154(b) by 220 days.

(21) Appl. No.: 12/997,686

(22) PCT Filed: May 26, 2009

(86) PCT No.: PCT/US2009/045131
§ 371 (c)(1), (2), (4) Date: Feb. 7, 2011

(87) PCT Pub. No.: WO2009/154953
PCT Pub. Date: Dec. 23, 2009

(65) Prior Publication Data
US 2011/0121176 A1    May 26, 2011

Related U.S. Application Data

(60) Provisional application No. 61/074,387, filed on Jun. 20, 2008.

(51) Int. Cl.
*H01J 37/26*    (2006.01)

(52) U.S. Cl.
USPC ........ 250/309; 250/306; 250/307; 250/492.3; 250/423 R (58) Field of Classification Search
USPC ............ 250/306, 307, 309, 310, 311, 423 R, 250/492.1, 492.3
See application file for complete search history.

(56) References Cited

U.S. PATENT DOCUMENTS

| | | | |
|---|---|---|---|
| 6,075,256 A | 6/2000 | Kaifu et al. | |
| 7,601,953 B2 | 10/2009 | Ward et al. | |
| 2003/0006388 A1* | 1/2003 | Ogawa | 250/591 |
| 2007/0138388 A1* | 6/2007 | Ward et al. | 250/288 |
| 2010/0294930 A1* | 11/2010 | Preikszas et al. | 250/307 |

FOREIGN PATENT DOCUMENTS

| | | |
|---|---|---|
| EP | 1 286 182 | 2/2003 |
| JP | H 9-298226 | 11/1997 |
| JP | 2009/517842 | 4/2009 |
| WO | WO 2007/067296 | 6/2007 |
| WO | WO 2007/067315 | 6/2007 |

OTHER PUBLICATIONS

Sakai et al., Contrast mechanisms in scanning ion microscope imaging for Metals, Applied Physics Letters, AIP, American Institute of Physics, Melville, NY, US, vol. 73, No. 5, Aug. 3, 1998, pp. 611-613.

(Continued)

*Primary Examiner* — Nicole Ippolito
(74) *Attorney, Agent, or Firm* — Fish & Richardson P.C.

(57) ABSTRACT

The disclosure relates to sample inspection using an ion-beam microscope. In some embodiments, the disclosure involves the use of multiple detectors, each of which provides different information about a sample.

29 Claims, 4 Drawing Sheets

(56) References Cited

OTHER PUBLICATIONS

Wouters, Buys Ballotlab Rijksunivutrecht Netherlands; Zeijlmans Vanemmichoven P A; Buys Ballotlab Rijksuniv Utrecht Neth: "Instrumentation and experimental procedure for investigation of the electronic and geometrical structure of metal surfaces" Measurement Science and Technology, IOP, Bristol, GB, vol. 1, No. 1, Jan. 1, 1990, pp. 41-49.

International Search Report and Written Opinion for corresponding PCT Appl. No. PCT/US2009/045131, dated Mar. 24, 2010.
McGuinness, P.E., "Seeing at Atomic Resolution is Beleiving: Welcome the Helium Ion Microscope", Scanning 27(6): 323 (2005).
Simson et al., "Detection of low-energy protons using a silicon drift detector," Nuclear Instruments and Methods in Physics Research A 581 (2007) 772-775.
Japanese Office Action, with translation thereof, for JP Appl No. 2011-514669, dated Aug. 13, 2013.

* cited by examiner

FIG. 4 ically, the photoresist is removed in one or more subsequent process steps, and, in general, the final semiconductor article desirably does not contain an appreciable amount of photoresist.

SAMPLE INSPECTION METHODS, SYSTEMS AND COMPONENTS

FIELD

The disclosure relates to sample inspection methods, systems and components.

BACKGROUND

Semiconductor fabrication typically involves the preparation of an article (a semiconductor article) that includes multiple layers of materials sequentially deposited and processed to form an integrated electronic circuit, an integrated circuit element, and/or a different microelectronic device. Such articles typically contain various features (e.g., circuit lines formed of electrically conductive material, wells filled with electrically non-conductive material, regions formed of electrically semiconductive material) that are precisely positioned with respect to each other (e.g., generally on the scale of within a few nanometers). The location, size (length, width, depth), composition (chemical composition) and related properties (conductivity, crystalline orientation, magnetic properties) of a given feature can have an important impact on the performance of the article. For example, in certain instances, if one or more of these parameters is outside an appropriate range, the article may be rejected because it cannot function as desired. As a result, it is generally desirable to have very good control over each step during semiconductor fabrication, and it would be advantageous to have a tool that could monitor the fabrication of a semiconductor article at various steps in the fabrication process to investigate the location, size, composition and related properties of one or more features at various stages of the semiconductor fabrication process. As used herein, the term semiconductor article refers to an integrated electronic circuit, an integrated circuit element, a microelectronic device or an article formed during the process of fabricating an integrated electronic circuit, an integrated circuit element, a microelectronic device. In some embodiments, a semiconductor article can be a portion of a flat panel display or a photovoltaic cell.

Regions of a semiconductor article can be formed of different types of material (electrically conductive, electrically non-conductive, electrically semiconductive). Exemplary electrically conductive materials include metals, such as aluminum, chromium, nickel, tantalum, titanium, tungsten, and alloys including one or more of these metals (e.g., aluminum-copper alloys). Metal silicides (e.g., nickel silicides, tantalum silicides) can also be electrically conductive. Exemplary electrically non-conductive materials include borides, carbides, nitrides, oxides, phosphides, and sulfides of one or more of the metals (e.g., tantalum borides, tantalum germaniums, tantalum nitrides, tantalum silicon nitrides, and titanium nitrides). Exemplary electrically semiconductive materials include silicon, germanium and gallium arsenide. Optionally, an electrically semiconductive material can be doped (p-doped, n-doped) to enhance the electrical conductivity of the material.

Typical steps in the deposition/processing of a given layer of material include imaging the article (e.g., to determine where a desired feature to be formed should be located), depositing an appropriate material (e.g., an electrically conductive material, an electrically semiconductive material, an electrically non-conductive material) and etching to remove unwanted material from certain locations in the article. Often, a photoresist, such as a polymer photoresist, is deposited/exposed to appropriate radiation/selectively etched to assist in controlling the location and size of a given feature. Typically, the photoresist is removed in one or more subsequent process steps, and, in general, the final semiconductor article desirably does not contain an appreciable amount of photoresist.

Semiconductor articles can be inspected using, for example, charged particles, such as electrons and/or ions. In some instances, to achieve such inspection, a cross-section of the article is made to expose an area of interest of the article, followed by the inspection process.

SUMMARY

The disclosure relates to sample detection methods, systems and components.

In some instances, it can be desirable to be able to obtain quantitative material constituent information for a sample. However, doing so can be time consuming. Further, it may on occasion be the case that there is no relevant material constituent information to be obtained. For example, it may be interesting to determine whether a region of interest of a semiconductor article is formed of the appropriate material (e.g., an electrically conductive material, an electrically insulating material) to determine whether an undesired short circuit or open circuit is present. After obtaining the material constituent information, it may be determined that there is no undesirable short circuit or open circuit. In this case, at least some of the relatively large amount of time consumed obtaining the quantitative material constituent information could have been saved if there were a more efficient approach to making an initial determination (e.g., a qualitative determination) regarding whether any significant material constituent information was likely to be obtained.

In some embodiments, the disclosure provides a process that involves three basic steps. In the first step, a determination is made whether a potential feature of interest is present at a region of interest of a sample. The first step is done in a relatively quick manner. Thus, if it is determined that a potential feature of interest is not present in the region of interest, a substantial amount of time can be saved. However, it may be the case that, while the first step can demonstrate whether a potential feature of interest is present, this step cannot distinguish between topographic and material constituent contributions to the feature. As an example, the first step can involve exposing the region of interest to an ion beam (e.g., generated by a gas field ion microscope) or an electron beam (e.g., generated by an electron microscope) and detecting secondary electrons from the sample, followed by creating an image from the detected secondary electrons and analyzing the image.

In the second step, which is often performed only if the first step indicates that a potential feature of interest is present at the region of interest, qualitative material constituent information is obtained about the feature. This step can be used to determine whether a change in material constituent is a substantial component of the potential feature of interest. This step may be slower than the first step but is generally substantially faster than the process of determining quantitative material constituent information about the sample. As a result, if it is determined that the potential feature of interest does not have a substantial component that is due to a change in material constituent, a substantial amount of time can be saved. As an example, the second step can involving exposing the sample to an ion beam and measuring the abundance of scattered ions.

In the third step, which is often performed only if the second step indicates that the feature has a substantial contribution that is due to a change in material constituent, quantitative information is obtained about the feature. The third step, which is typically the slowest step, can be avoided in cases where there is no feature of interest (e.g., no undesired open circuit, no undesired closed circuit) or where there is a feature of interest but the feature does not have a substantial component that is due to a change in material constituent (e.g., the feature is due primarily to the topography of the surface of the sample).

As referred to herein, a scattered ion is generated when an ion from the ion beam (e.g., a He ion) interacts with the sample and is scattered from the sample while remaining an ion (e.g., a He ion). Because the probability that a scattered ion can travel from the sub-surface region of a sample to the surface of the sample and then be emitted from the sample is very low, scattered ions generally provide information about the surface of the sample. As explained in more detail below, when detecting scattered ions, the particular arrangement of the detector(s) generally depends on the type of information that is desired to be obtained.

A secondary electron, as referred to herein, is an electron that is emitted from a sample species and that has an energy of less that 50 eV. In general, secondary electrons are emitted from the sample surface at a range of angles and energies. However, the information of most interest is usually the total abundance of secondary electrons (as opposed to energy-resolved secondary electron information, or angle-resolved secondary electron information) because, as explained below, the total abundance of the secondary electrons is what can provide information regarding the sample surface.

In one aspect, the disclosure features a method that includes detecting electrons generated from a sample, detecting an abundance of a first plurality ions scattered from the sample, and detecting a second plurality of ions scattered from the sample based on energy of the second plurality of ions.

In another aspect, the disclosure features a method that includes generating ions with a gas field ion source, and interacting the ions with a sample to generate electrons. The method also includes detecting the electrons for a first period of time, and forming a first image based on the detected electrons. The method further includes, after detecting the electrons, detecting an abundance of a first plurality ions scattered from the sample for a second period of time, and forming a second image based on the first plurality of scattered ions. In addition, the method includes, after detecting the first plurality of scattered ions, detecting a second plurality of ions scattered from the sample based on energy of the second plurality of ions for a third period of time. The second period of time is greater than the first period of time, and the third period of time is greater than the second period of time.

In an additional aspect, the disclosure features a method that includes generating ions with a gas field ion source, and interacting the ions with a sample to generate electrons. The method further includes detecting the electrons, and forming a first image based on the detected electrons. In addition, the method includes, after detecting the electrons, detecting an abundance of a first plurality ions scattered from the sample, and forming a second image based on the first plurality of scattered ions. The method also includes, after detecting the first plurality of scattered ions, detecting a second plurality of ions scattered from the sample based on energy of the second plurality of ions. The region of the sample from which the second plurality of ions is detected is based on the first image and/or the second image.

In one aspect, the disclosure features a system that includes a housing configured to house a sample, and a charged particle source in the housing. The system also includes a first detector configured to detect electrons generated at the sample, and a second detector configured to detect an abundance of ions scattered from the sample. The system further includes a third detector configured to detect ions scattered from the sample based on energy of the ions. The first, second and third detectors are different detectors, and the first second and third detectors are in the housing.

In another aspect, the disclosure features a system that includes a housing configured to house a sample, and a gas field ion source in the housing. The system also includes an Everhart-Thornley detector configured to detect electrons generated at the sample, where the Everhart-Thornley detector is in the housing. The system further includes a microchannel plate detector configured to detect an abundance of ions scattered from the sample, where the microchannel plate detector is in the housing. In addition, the system includes a solid state detector configured to detect ions scattered from the sample based on energy of the ions, where the solid state detector is in the housing.

In a further aspect, the disclosure features a method that includes obtaining a first set of information about a sample from which topographical sample information cannot be distinguished from sample constituent information, and obtaining a second set of information about the sample that provides qualitative material constituent information about the sample. The method also includes obtaining a third set of information about the sample that provides quantitative material constituent information about the sample.

In an additional aspect, the disclosure features a method that includes detecting a plurality of first particles from a sample for a first period of time, and then, detecting a first plurality of second particles from the sample for a second period of time. The second particles are different from the first particles, and the second period of time is greater than the first period of time. The method further includes then detecting a second plurality of the second particles from the sample for a third period of time. The second plurality of the second particles are different from the first plurality of the second particles, and the third period of time are greater than the second period of time.

In one aspect, the disclosure features a method that includes generating a beam of electrons, and interacting the beam of electrons with a sample to generate secondary electrons. The method also includes detecting the secondary electrons for a first period of time, and forming a first image based on the detected electrons. The method further includes, after detecting the electrons, detecting an abundance of a first plurality ions scattered from the sample for a second period of time, and forming a second image based on the first plurality of scattered ions. In addition, the method includes, after detecting the first plurality of scattered ions, detecting a second plurality of ions scattered from the sample based on energy of the second plurality of ions for a third period of time. The second period of time is greater than the first period of time, and the third period of time is greater than the second period of time.

In another aspect, the disclosure features an article that includes an electrically conductive layer, an inactive region, and a detection region. The inactive region is between the electrically conductive layer and the detection region. The electrically conductive layer has a thickness of at most 25 nm, and the article is a solid state detector.

In a further aspect, the disclosure features an article that includes an electrically conductive region, an inactive region, and a detection region. The inactive region is between the electrically conductive region and the detection region. The inactive region has a thickness of at most 25 nm, and the article is a solid state detector.

In an additional aspect, the disclosure features an article that includes an electrically conductive mesh, an inactive region, and a detection region. The inactive region is between the electrically conductive mesh and the detection region. The article is a solid state detector.

In one aspect, the disclosure features an article that includes an electrically conductive mesh, an inactive region, and a detection region. The inactive region is between the electrically conductive mesh and the detection region. The article is a solid state detector.

The disclosure can provide relatively quick and efficient methods and systems for inspecting samples.

Other features and advantages will be apparent from the description, drawings, and claims.

DETAILED DESCRIPTION

Figure 1:
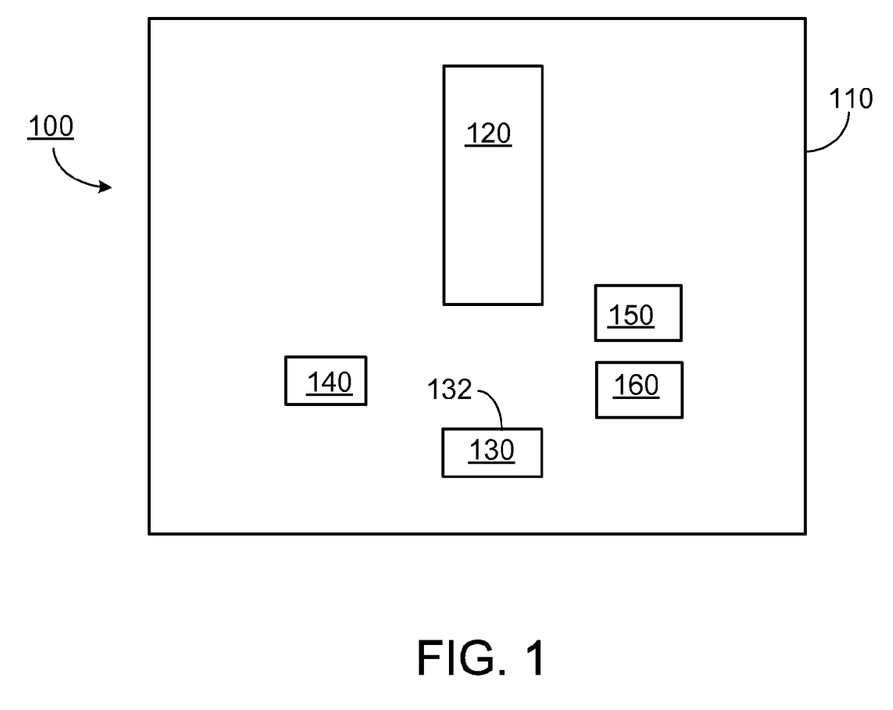
FIG. 1 is a schematic representation of a gas field ion microscope.

FIG. 1 shows an exemplary gas field ion microscope 100 that includes a housing 110, a gas field ion system 120, a sample 130 and detectors 140, 150 and 160. System 120 creates an ion beam that impinges on a surface 132 of sample 130, causing ions to scatter from sample 130 and also causing secondary electrons to leave sample 130. Detector 140 (e.g., an Everhart-Thornley detector) detects the secondary electrons. Detector 150 (e.g., a microchannel plate detector) detects an abundance of the ions scattered from surface 132, and detector 160 (e.g., a solid state detector) detects ions scattered from surface 132 in an energy-resolved and angle-resolved fashion.

Figure 2:
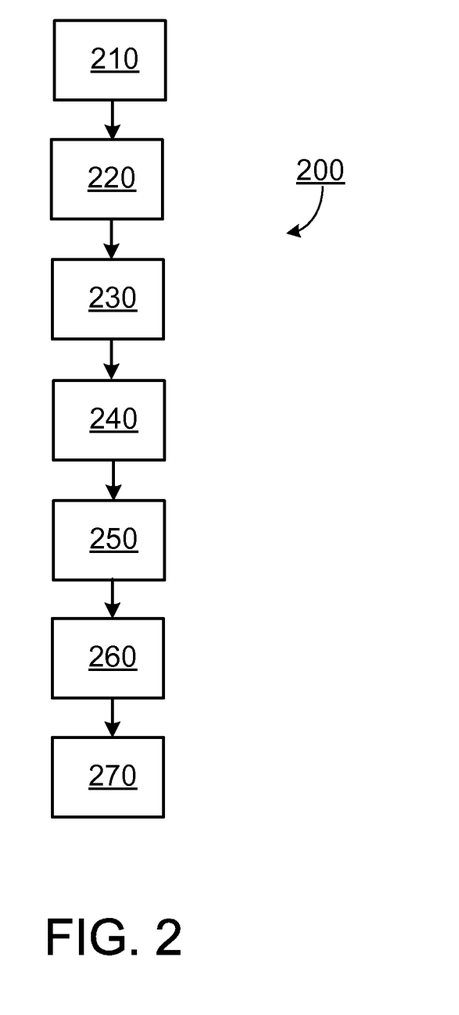
FIG. 2 is a flowchart of a process for inspecting a sample.

FIG. 2 shows a flow chart of a process 200 for using microscope 100 to determine information about sample 130. In step 210, detector 140 detects secondary electrons, and according to step 220 an image of sample 130 is created based on the detected secondary electrons. With step 230, the image is evaluated to determine whether a potential feature of interest is present (e.g., at surface 132 of sample 130).

Often, it may not be possible to determine whether a potential feature that appears in the secondary electron image is due to a topographical feature (e.g., one or more hills, one or more bumps) at surface 132, a changed material constituents at or near surface 132, or both. As described below, however, subsequent steps in the process can provide information that assists in determining whether a potential feature is at least partially due to a change in material constituent at or near surface 132.

In step 240, detector 150 detects an abundance of scattered ions from sample 130. Optionally, in step 240, the scattered ions can be detected from a region of sample 130 that is a subset of the region of sample 130 from which secondary electrons are detected in step 210. For example, if in step 230 it is determined that a feature of potential interest is present at a particular location of sample 130, then in step 240 scattered ions may be collected only from a region of sample 130 adjacent the feature of potential interest. Alternatively, substantially the same region of sample 130 may be investigated in steps 210 and 240. According to step 250, the total abundance of scattered ion information is processed to provide qualitative material constituent information about sample 130. The qualitative information can indicate, for example, if there is a change in the material(s)/element(s) present at or near surface 132 where the feature of potential interest is present.

According to step 260, detector 160 detects scattered ions in an energy-resolved and angle-resolved fashion. In step 270, this information is processed to provide quantitative information regarding material constituent at or near surface 132.

While the foregoing process includes each of steps 210 through 270, in some embodiments, the process may be terminated at various points. As an example, the process can be terminated after step 230. This may be desirable, for example, if it is determined in step 230 that sample 130 lacks a potential feature of interest. As another example, the process can be terminated after step 250. This may be desirable if, for example, the information processed in step 250 leads to the conclusion that there is little or no contribution to the feature from material constituent changes.

In some embodiments, the time to detect the secondary electrons is small compared to the time to detect the abundance of scattered ions. For example, in certain embodiments, the time to detect abundance of scattered ions is at least 10 times (e.g., at least 50 times, at least 100 times) as long as the time to detect the secondary electrons.

In certain embodiments, the time to detect scattered ions in an energy-resolved and angle-resolved manner is at least 0.1 times (e.g., at least one time, at least 10 times) as long as the time to detect the abundance of scattered ions.

Particle Detection

Certain aspects of particle detection are described below.

(i) Secondary Electrons

Detecting the total abundance of secondary electrons can provide information regarding the topography of a sample. The secondary electron total abundance at a given location on a surface generally depends upon the slope of the surface relative to the ion beam at that point. In general, the secondary electron total abundance is higher where the slope of the surface relative to the ion beam is higher (i.e., where the angle of incidence of the ion beam as measured from the surface normal is larger). Thus, the change in the total abundance of secondary electrons as a function of the location of the ion beam on the surface of the sample, can be correlated to a change in the slope of the surface, providing information regarding the topography of the surface of the sample.

Detecting the total abundance of secondary electrons can also yield material constituent information (e.g., elemental information, chemical environment information) about a sample. In such embodiments, the information is predominantly related to the surface of the sample. In general, each element or material in a given chemical environment will have a particular inherent secondary electron yield. As a result, the secondary electron total abundance at a given location on a surface generally depends on the material present at that location. Therefore, the change in the total abundance of secondary electrons as a function of the location of the ion beam on the surface of the sample, can be correlated to a change in the element(s) and/or material(s) present at the surface of the sample, providing material constituent information about the surface of the sample.

(ii) Scattered Ion Abundance

The total abundance of scattered ions can be used to determine qualitative material constituent information because, in general, the scattering probability of an ion, such as a He ion, (and therefore the total abundance of scattered ions, assuming no effects from other factors, such as topographical changes in the surface sample) is approximately proportional to the square of the atomic number (Z value) of the surface atom from which the ion scatters. Thus, as an example, when using He ions and trying to distinguish a copper (atomic number 29) line from silicon (atomic number 14) in a semiconductor article, the total abundance of scattered He ions from a copper atom at a surface of the semiconductor article will be approximately four times the total abundance of scattered ions from a silicon atom at the surface of the semiconductor article. As another example, when using He ions trying to distinguish a tungsten (atomic number 74) plug from silicon (atomic number 14) in a semiconductor article, the total abundance of scattered He ions from a tungsten atom at a surface of the semiconductor article will be approximately 25 times the total abundance of scattered ions from a silicon atom at the surface of the semiconductor article. As a further example, when using He ions trying to distinguish gold (atomic number 79) region from silicon (atomic number 14) in a semiconductor article, the total abundance of scattered He ions from a gold atom at a surface of the semiconductor article will be approximately 25 times the total abundance of scattered ions from a silicon atom at the surface of the semiconductor article. As an additional example, when using He ions and trying to distinguish indium (atomic number 49) from silicon (atomic number 14) in a semiconductor article, the total abundance of scattered He ions from a indium atom at a surface of the semiconductor article will be approximately 10 times the total abundance of scattered ions from a silicon atom at the surface of the semiconductor article.

The total abundance of scattered ions can be detected using a single detector (e.g., a hemispherical detector) configured to detect scattered ions leaving the surface of a sample, or multiple detectors (e.g., located at different solid angles with respect to the surface of the sample) configured to detect scattered ions leaving the surface (iii) Energy-Resolved and Angle-Resolved Scattered Ion Detection Energy-resolved and angle-resolved scattered ion detection can be used to determine quantitative material constituent information about the surface of a sample. The detector is designed so that the angle and energy of each detected scattered ion is known for each angle within the acceptance angle of detector. Using He ions as an example, by measuring the energy and scattering angle of the scattered He ion, the mass of the atom at the surface that scatters the scattered He ion can be calculated based on the following relationship:

$$\frac{E_s}{E_i} = 1 - \frac{2M_{He}M_a}{(M_{He}M_a)^2}(1 - \cos\theta_s)$$

where $E_s$ is the energy of the scattered He ion, $E_i$ is the incident energy of the He ion, $M_{He}$ is the mass of the He ion, $\theta_s$ is the scattering angle, and $M_a$ is the mass of the atom that scatters the He ion.

The detector can, for example, be an energy-resolving phosphor-based detector, an energy-resolving scintillator-based detector, a solid state detector, an energy-resolving electrostatic prism-based detector, an electrostatic prism, an energy-resolving ET detector, or an energy-resolving microchannel. In general, it is desirable for the detector to have a substantial acceptable angle. In some embodiments, the detector is stationary (e.g., an annular detector). In certain embodiments, the detector can sweep through a range of solid angles. Although a system for detecting energy-resolved and angle-resolved scattered ions that includes a single detector has been described above, such a system can contain multiple (e.g., two, three, four, five, six, seven, eight) detectors. Often, the use of multiple detectors is desirable because it can allow for a larger acceptance angle of detected scattered ions.

Additional aspects of particle detection are described, for example, in US 2007-0158558, which is hereby incorporated by reference in its entirety.

Detectors

Certain exemplary detectors and arrangements of detectors are described below.

(i) Everhart-Thornley Detectors

An Everhart-Thornley (ET) detector can be used to detect secondary electrons, ions, and/or neutral particles. Such detectors are described, for example, in US 2007-0158558. Briefly, an ET detector can include a particle selector, a conversion material, a support, a photon detector, and two voltage sources. The particle selector is typically formed of an electrically conductive material. In some embodiments, for example, the particle selector can be from any open electrode structure that includes a passage for particles to pass through, such as a grid, a mesh, a ring or a tube. Particle selector 601 can be formed from one or more electrodes, and potentials applied to the one or more electrodes can generally be selected as desired according to the type of particles being measured. The conversion material is formed of a material that, upon interaction with a charged particle (e.g., an ion, an electron) can form a photon. Exemplary materials include phosphor materials and/or scintillator materials (e.g., crystalline materials, such as yttrium-aluminum-garnet (YAG) and yttrium-aluminum-phosphate (YAP). The support is usually formed of a material that is relatively transparent to photons formed by conversion material. During operation, a first voltage source applies a voltage of relatively small magnitude (e.g., 500 V or less, such as from 100 V to 500 V) to the particle selector, and a second voltage source applies a voltage of relatively large magnitude (e.g., 5 kV or more, 10 kV or more) to the conversion material. Typically, during electron detection, the sign of the voltage applied to the particle selector and conversion material is positive with respect to the sample. Usually, when detecting ions, the sign of the voltage applied to the particle selector and the conversion material is negative with respect to the sample. In certain embodiments, the sample can also be biased (with respect to the common external ground) to assist in delivering particles from the sample to the detector. Charged particles (e.g., electrons or ions) from the sample are attracted to the particle selector, pass through the particle selector, and are accelerated toward the conversion material. The charged particles then collide with the conversion material, generating photons. The photons pass through the support and are detected by the photon detector.

(ii) Microchannel Plate Detectors

In some embodiments, a microchannel plate detector can be used to amplify a flux of secondary electrons, neutral atoms, or ions from a sample. Microchannel plates are typically formed from materials such as fused silica, and generally include a large number of small diameter channels arranged in the form of an array. Particles enter individual channels and collide with channel walls, generating free electrons. Typically, multiple free electrons are generated on each collision of a particle (neutral atom, ion, or electron) with a channel wall. As a result, a cascaded electron signal corresponding to an amplification of the input particle signal exits the microchannel plate.

Microchannel plate-based detectors (which can include one or more microchannel plates) can be configured to detect ions, secondary electrons, and/or neutral atoms from the sample. Neutral particles and/or ions (e.g., secondary ions and atoms, scattered ions and primary atoms) formed from the sample typically leave the surface of the sample (the surface on which the ion beam impinges).

Microchannel plates amplify an incoming particle signal and convert the incoming signal to an outgoing electron signal. To visualize the outgoing electron signal, microchannel plate-based detectors can also include a conversion material, a screen, and a photon detector (see discussion above).

(iii) Conversion Plates

In some embodiments, a conversion plate can be used to detect ions (e.g., scattered ions, secondary ions) from the sample or neutral particles (e.g., primary neutral He atoms in the case where He ions are the primary constituent of the ion beam) from the sample. Typically, a conversion plate can be formed from a thin foil material that, when struck by an incident ion or atom, has a high secondary electron yield. An example of such a material is platinum.

(iv) Channeltron Detectors

Channeltron detectors can also be used to detect particles such as electrons, ions and neutral atoms leaving the sample. Channeltron detectors function by amplifying particle signals through multiple internal collisions in a manner similar to that described in connection with microchannel plate detectors. Measurement of relatively weak secondary electron, ion, or neutral atom fluxes from the sample is possible by measuring the amplified particle signals that are output by a channeltron detector.

(v) Phosphor Detectors

Phosphor-based detectors, which include a thin layer of a phosphor material deposited atop a transparent substrate, and a photon detector such as a CCD camera, a PMT, or one or more diodes, can be used to detect electrons, ions and/or neutral particles from the sample. Particles strike the phosphor layer, inducing emission of photons from the phosphor which are detected by the photon detector.

(vi) Solid State Detectors

Solid state detectors can be used to detect secondary electrons, ions, and/or neutral atoms from the sample. A solid state detector can be constructed from a sensor formed of a material such as silicon, or a doped silicon material. The number of electron-hole pairs generated by an incident particle, and therefore the corresponding magnitude of the current produced, depends in part upon the particle's energy. Thus, a solid state detector can be particularly useful for energy measurements of particles, which can be especially advantageous when detecting high energy particles (e.g., scattered He ions and neutral He atoms in the case where He ions are the primary constituent of the ion beam) from the sample. An example of a solid state detector is a silicon drift detector.

Figure 4:
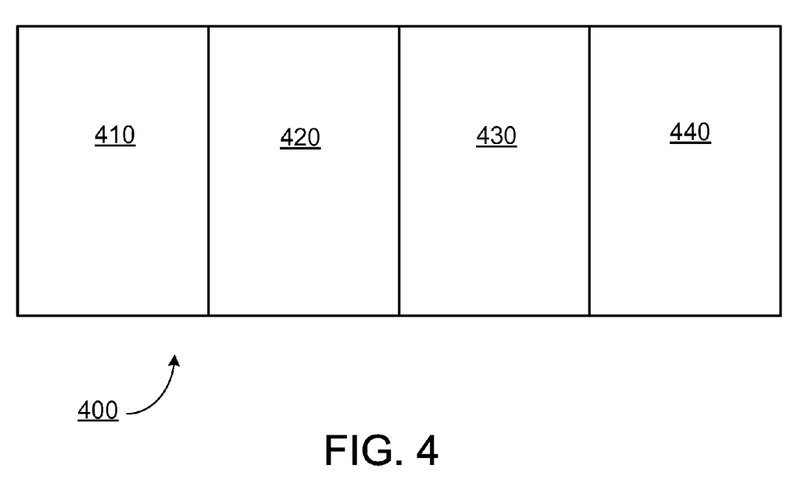
FIG. 4 is a schematic representation of a solid state detector.

In some embodiments, a solid state detector may be windowless. In some embodiments, a solid state detector may have a relatively thin electrically conductive layer. FIG. 4 is a schematic representation of a windowless solid state detector 400 having a layer 410, an inactive region 420, a detection region 430, and a substrate 440. Typically, layer 410 is formed of an electrically conductive material, such as a metal (e.g., aluminum, copper, gold, silver, nickel, platinum, palladium) or an alloy. Often, layer 410 is a metallization layer (e.g., formed by physical vapor deposition or chemical vapor deposition). In general, layer 420 is formed of a doped semiconductor (e.g., doped silicon). Layer 430 is generally formed of an undoped or lightly doped semiconductor e.g., lightly doped silicon, undoped silicon).

Without wishing to be bound by theory, it is believed that a relatively thin metallization layer can reduce energy loss (e.g., via phonon creation) of the ions within the metallization layer and/or that a relatively thin metallization layer can reduce the possibility of ions entering the detector but not reaching the detection region of the detector (e.g., by one or more scattering processes within the metallization layer and/or the inactive silicon layer). In some embodiments, metallization layer 410 is less than 30 nm thick (e.g., less than 25 nm thick, less than 20 nm thick, less than 15 nm thick, less than 10 nm thick), and/or more than one nm thick (e.g., more than five nm thick). In certain embodiments, layer 420 is relatively thin. For example, layer 430 can be less 30 nm thick (e.g., less than 25 nm thick, less than 20 nm thick, less than 15 nm thick, less than 10 nm thick), and/or more than one nm thick (e.g., more than five nm thick).

Although embodiments have been described in which layer 410 is present, in some embodiments, a mesh or grid can be used instead of a layer. The materials are general the same as noted above, and the mesh or grid can optionally be a metallization layer (e.g., formed by physical vapor deposition, chemical vapor deposition). In certain embodiments, the mesh or grid can be printed (e.g., using ink jet printing).

(vii) Scintillator Detectors

Similar to phosphor-based detectors, scintillator-based detectors include a scintillator material that generates photons in response to being struck by an incident particle (electron, ion, or neutral atom). Suitable scintillator materials include, for example, YAG and YAP. The photon yield in scintillator-based detectors depends on the energy of the incident particles. As a result, a scintillator detector can be particularly useful for energy measurements of particles, which can be especially advantageous when detecting high energy particles (e.g., scattered He ions and neutral He atoms in the case where He ions are the primary constituent of the ion beam) from the sample.

(viii) Energy Detectors for Ions

A variety of different detectors and detection schemes can be implemented to measure energies of ions (e.g., scattered He ions in the case where He ions are the primary constituent of the ion beam) from the sample. Electrostatic prism detectors, in which an electric and/or magnetic field is used to deflect incident ions, where the amount of deflection depends on the energy of the ions, can be used to spatially separate ions with different energies. Magnetic prism detectors may also be used to spatially separate ions based on the energy of the ions. Any of the suitable detectors discussed above (e.g., microchannel plates, channeltrons, and others) can then be used to detect the deflected ions.

Quadrupole detectors can also be used to analyze energies of ions from the sample. In a quadrupole detector, a radio-frequency (RF) field within the quadrupole ensures that ions having a chosen mass and energy propagate along a straight, undeflected trajectory within the quadrupole. Ions with a different mass and/or energy propagate along a curved trajectory within the quadrupole. From the deflected position of ions within the quadrupole analyzer, energies of the ions can be determined.

In some embodiments, ion energy can be determined by placing a positively biased particle selector (e.g., a screen or mesh of electrically conductive material, or a cylindrical metal tube or ring) along the flight path of the ions and in front of the detector. The magnitude of the electrical potential applied to the particle selector can initially be very high (e.g., a value certain to prevent ions from the sample from passing therethrough), and the magnitude of the electrical potential can be reduced while using an appropriate detector (see discussion above) to detect the ions. The current of ions that reach the detector as a function of the magnitude of the potential bias on the particle selector can be used to determine information about the energy of the ions.

(ix) Energy Detectors for Electrons

A variety of different detectors and detection schemes can be implemented to measure energies of electrons (e.g., secondary electrons) from the sample. Prism detectors, in which an electric and/or magnetic field is used to deflect incident electrons, and where the amount of deflection depends on the energy of the electrons, can be used to spatially separate electrons with different energies. Any of the suitable detectors discussed above can then be used to detect the deflected electrons.

In some embodiments, electron energies can be determined by placing a negatively biased particle selector (e.g., a screen or mesh of electrically conductive material, or a cylindrical metal tube or ring) along the flight path of the electrons and in front of the detector. The magnitude of the electrical potential of the particle selector can initially be very high (e.g., a value certain to prevent the electrons from the sample from passing therethrough), and the magnitude of the electrical potential can be reduced while using an appropriate detector (see discussion above) to detect the electrons. The electron current that reaches the detector as a function of the magnitude of the applied electrical potential on the particle selector can be used to determine information about the energies of the electrons.

(x) Angle-Dependent Measurements

Typically, to acquire angle-dependent information, a detector is affixed to a mount (e.g., a swivel mount) that permits movement of the detector throughout a range of solid angles about the sample. At a given orientation with respect to the sample that corresponds to a particular solid angle, abundance and/or energy measurements of particles are recorded. The detector is sequentially re-positioned at different solid angles and the measurements are repeated to determine the angular dependence of the measured quantities. In some embodiments, a limiting aperture such as a pinhole can be placed in front of the detector in the path of the scattered particles to further restrict the range of angles over which measurement of particles from the sample occurs.

Additional detectors and arrangements of detectors are described, for example, in US 2007-0158558.

Gas Field Ion Microscope

Typically, system 120 includes a gas source, a gas field ion source and ion optics.

In general, the gas field ion source includes an electrically conductive tip (typically having an apex with 10 or fewer atoms) that can be used to ionize neutral gas species to generate ions (e.g., in the form of an ion beam) by bringing the neutral gas species into the vicinity of the electrically conductive tip (e.g., within a distance of about four to five angstroms) while applying a high positive potential (e.g., one kV or more relative to the extractor (see discussion below)) to the apex of the electrically conductive tip. The electrically conductive tip can be formed of various materials. In some embodiments, tip 186 is formed of a metal (e.g., tungsten (W), tantalum (Ta), iridium (Ir), rhenium (Rh), niobium (Nb), platinum (Pt), molybdenum (Mo)). In certain embodiments, the electrically conductive tip can be formed of an alloy. In some embodiments, the electrically conductive tip can be formed of a different material (e.g., carbon (C)).

During use, the electrically conductive tip is biased positively (e.g., approximately 20 kV) with respect to an extractor, and the extractor is negatively or positively biased (e.g., from −20 kV to +50 kV) with respect to an external ground. Optionally, a suppressor is biased positively or negatively (e.g., from −5 kV to +5 kV) with respect to the electrically conductive tip. Because the tip is formed of an electrically conductive material, the electric field of the tip at the tip apex points outward from the surface of the tip apex. Due to the shape of the tip, the electric field is strongest in the vicinity of the tip apex. The strength of the electric field of the tip can be adjusted, for example, by changing the positive voltage applied to the tip. With this configuration, un-ionized gas atoms supplied by a gas source are ionized and become positively-charged ions in the vicinity of the tip apex. The positively-charged ions are simultaneously repelled by the positively charged tip and attracted by the negatively charged extractor such that the positively-charged ions are directed from the tip into ion optics as an ion beam. Optionally a suppressor assists in controlling the overall electric field between the tip and the extractor and, therefore, the trajectories of the positively-charged ions from the tip to the ion optics. In general, the overall electric field between the tip and the extractor can be adjusted to control the rate at which positively-charged ions are produced at the tip apex, and the efficiency with which the positively-charged ions are transported from the tip to the ion optics.

In general, the ion optics are configured to direct the ion beam onto surface 132 of sample 130. The ion optics can, for example, focus, collimate, deflect, accelerate, and/or decelerate ions in the ion beam. The ion optics can also allow only a portion of the ions in the ion beam to pass through the ion optics. Generally, the ion optics include a variety of electrostatic and other ion optical elements that are configured as desired. By manipulating the electric field strengths of one or more components (e.g., electrostatic deflectors) in the ion optics, the ion beam can be scanned across surface 132 of sample 130. For example, the ion optics can include two deflectors that deflect the ion beam in two orthogonal directions. The deflectors can have varying electric field strengths such that the ion beam is rastered across a region of surface 132.

The gas source is usually configured to supply one or more gases to the gas field ion source. The gas source 110 can be configured to supply the gas(es) at a variety of purities, flow rates, pressures, and temperatures. In general, at least one of the gases supplied by the gas source is a noble gas (helium (He), neon (Ne), argon (Ar), krypton (Kr), xenon (Xe)), and ions of the noble gas are desirably the primary constituent in the ion beam. Often, gas supplied by the gas source is primarily He, Ne, Ar, Kr or Xe.

Optionally, the gas source can supply one or more gases in addition to the noble gas(es), an example of such a gas is nitrogen. Typically, while the additional gas(es) can be present at levels above the level of impurities in the noble gas(es), the additional gas(es) still constitute minority components of the overall gas mixture introduced by the gas source.

During use, the ion beam is directed through the ion optics to surface 132 of sample 130. When the ion beam impinges on sample 130, a variety of different types of particles can be produced. These particles include, for example, secondary electrons, Auger electrons, secondary ions, secondary neutral particles, primary neutral particles, scattered ions and photons (e.g., X-ray photons, IR photons, visible photons, UV photons). Detectors 140, 150 and/or 160 are positioned and configured to each measure one or more different types of particles resulting from the interaction between the ion beam and sample 130 as noted above. As discussed above, the information measured by the detectors is used to determine information about sample 130. By rastering the ion beam across surface 132, pixel-by-pixel information about sample 130 can be obtained in discrete steps. Detectors 140, 150 and/or 160 can be configured to detect one or more different types of particles at each pixel.

The operation of microscope 100 is typically controlled via an electronic control system. For example, the electronic control system can be configured to control the gas(es) supplied by the gas source, the temperature of the tip, the electrical potential of the tip, the electrical potential of the extractor, the electrical potential of the suppressor (when used), the settings of the components of the ion optics, the position of the sample manipulator, and/or the location and settings of detectors 140, 150 and/or 160. Optionally, one or more of these parameters may be manually controlled (e.g., via a user interface integral with the electronic control system). Additionally or alternatively, the electronic control system can be used (e.g., via an electronic processor, such as a computer) to analyze the information collected by detectors 140, 150 and/or 160 and to provide information about sample 130 (e.g., topography information, material constituent information), which can optionally be in the form of an image, a graph, a table, a spreadsheet, or the like. Typically, the electronic control system includes a user interface that features a display or other kind of output device, an input device, and a storage medium.

In certain embodiments, the electronic control system can be configured to control various properties of the ion beam. For example, the control system can control a composition of the ion beam by regulating the flow of gases into the gas field ion source. By adjusting various potentials in the ion source and the ion optics, the control system can control other properties of the ion beam such as the position of the ion beam on sample 130, and the average energy of the incident ions.

In some embodiments, the electronic control system can be configured to control additional devices. For example, the electronic control system can be configured to regulate a supply of water molecules delivered to a region surrounding sample 130 and/or in a region of the ion beam. Alternatively, or additionally, the electronic control system can be configured to control heating and/or cooling devices which can be used in the formation and/or removal of ice layers. Further, in certain embodiments, the electronic control system can be configured to control one or more additional particle beams in addition to the ion beam. Additional particle beams can be used for sample imaging and/or sample modification (e.g., etching, milling).

In general, detectors 140, 150 and/or 160 are configured in accordance with particles to be measured, the measurement conditions and the desired information.

Gas field ion microscopes, as well as related components and methods, are generally disclosed, for example, in US 2007-0158558.

Computer Hardware and Software

In general, any of the methods (or portions thereof, such as control steps) described above can be implemented in computer hardware or software, or a combination of both. The methods can be implemented in computer programs using standard programming techniques following the methods and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The methods or portions thereof can also be implemented as a computer-readable storage medium, configured with a computer program, where the storage medium so configured causes a computer to operate in a specific and predefined manner to perform the functions described herein.

Other Embodiments

While certain embodiments have been described, other embodiments are possible.

As an example, while examples have been described in which a gas field ion source is used, other types of ion sources may also be used. In some embodiments, a liquid metal ion source can be used. An example of a liquid metal ion source is a Ga ion source (e.g., a Ga focused ion beam column).

As a further example, while embodiments have been described in which an ion source is used to create ions that impinge on a sample to cause secondary electrons to leave the sample, more generally, any charged particle source may be used to cause secondary electrons to leave the sample. For example, an electron source, such as a scanning electron microscope may be used. In such embodiments, an electron source may be used to collect an image based on detected secondary electrons, while an ion beam source (e.g., a gas field ion microscope) is used to detect scattered ions.

Figure 3A:
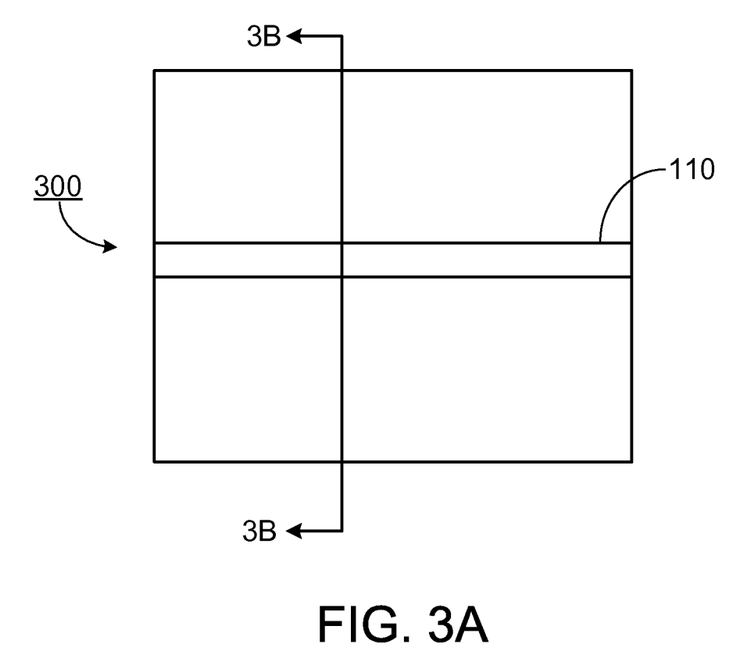
FIGS. 3A and 3B show partial top and cross-sectional views, respectively, of a semiconductor article having a cut cross-section.
Figure 3B:
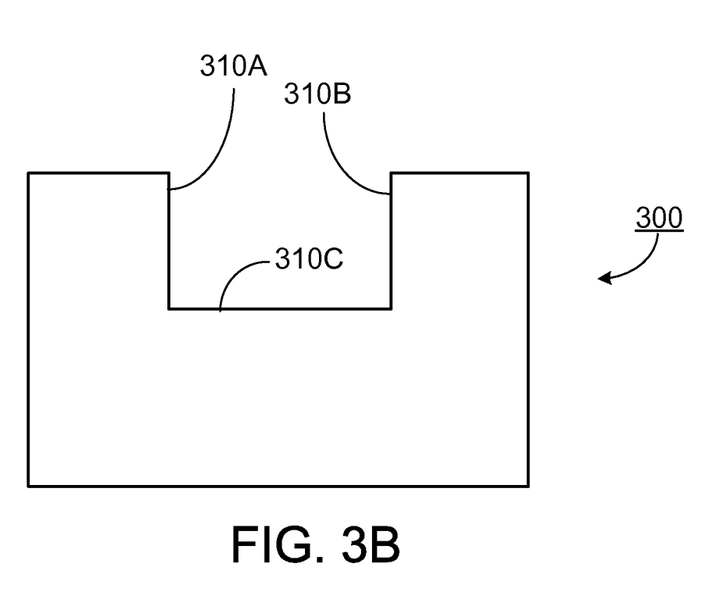

As yet a further example, while embodiments have been described which depict an upper surface of a sample being inspected, other surfaces of a sample may also be inspected. In some embodiments, a cross-section of a sample may be inspected. FIGS. 3A and 3B show partial top and cross-sectional views, respectively of a semiconductor article 300. As shown in FIG. 3B, article 300 has been cut to expose a cross-section 310 with sidewalls 310A and 310B and bottom wall 310C. Although not shown in FIGS. 3A and 3B, semiconductor article 300 includes many layers of different materials, and, in some instances, multiple different materials within the same layer. An ion beam and/or electron beam may be used to inspect sidewalls 310A and/or 310B, and or bottom wall 310C.

As another example, while embodiments have been disclosed in which a sample is inspected, alternatively or additionally, the systems and methods can be used to modify (e.g., repair) a sample (e.g., to repair a region of the article at or near the portion of the article exposed by the cross-section). Such modification can involve gas assisted chemistry, which can be used to add material to and/or remove material to a sample (e.g., a given layer of the sample). As an example, gas assisted chemistry can be used for semiconductor circuit editing in which damaged or incorrectly fabricated circuits formed in semiconductor articles are repaired. Typically, circuit editing involves adding material to a circuit (e.g., to close a circuit that is open) and/or removing material from a circuit (e.g., to open a circuit that is closed). Gas assisted chemistry can also be used in photolithographic mask repair. Mask defects generally include an excess of mask material in a region of the mask where there should be no material, and/or an absence of mask material where material should be present. Thus, gas assisted chemistry can be used in mask repair to add and/or remove material from a mask as desired. Typically, gas assisted chemistry involves the use of a charged particle beam (e.g., ion beam, electron beam, both) that interacts with an appropriate gas (e.g., $Cl_2$, $O_2$, $I_2$, $XeF_2$, $F_2$, $CF_4$, $H_2O$, $XeF_2$, $F_2$, $CF_4$, $WF_6$). As another example, modification of a sample can involve sputtering. In some instances, when fabricating articles, it can be desirable during certain steps to remove materials (e.g., when removing undesired material from a circuit to edit the circuit, when repairing a mask). An ion beam can be used for this purpose where the ion beam sputters material from the sample. In particular, an ion beam generated via the interaction of gas atoms with a gas field ion source as described herein can be used for sputtering a sample. Although He gas ions may be used, it is typically preferable to use heavier ions (e.g., Ne gas ions, Ar gas ions, Kr gas ions, Xe gas ions) to remove material. During the removal of material, the ion beam is focused on the region of the sample where the material to be removed is located. Examples of such inspection are disclosed, for example, in US 2007-0158558.

As an additional example, while embodiments have been described in which samples are in the form of semiconductor articles, in some embodiments, other types of samples can be used. Examples include biological samples (e.g., tissue, nucleic acids, proteins, carbohydrates, lipids and cell membranes), pharmaceutical samples (e.g., a small molecule drug), frozen water (e.g., ice), read/write heads used in magnetic storage devices, and metal and alloy samples. Exemplary samples are disclosed in, for example, US 2007-0158558.

As another example, while embodiments have been described in which secondary electrons are detected, more generally, the disclosure relates to the detection of any type of electron that leaves a sample. In some embodiments, the detected electrons can include Auger electrons. In certain embodiments, the detected electrons have an energy in excess of 50 eV.

As a further example, while certain embodiments have been described in which a single detector is shown for detecting a given set of information (secondary electrons, abundance of scattered ions, energy-resolved and angle-resolved scattered ions), more generally one or more detectors may be used to detect some or all of this information.

As another example, in some embodiments, the electrons that are detected pass through at least a portion of (e.g., all of) the optics used to focus the charged particle beam onto the sample (e.g., the ion optics in the case of a gas field ion microscope). Because such optics typically include one or more lenses, such detection configurations are often referred to as through lens detectors.

In general, various aspects of the foregoing embodiments can be combined as desired.

Other embodiments are covered by the claims.

What is claimed is:

1. A method, comprising:
    detecting electrons generated from a sample for a first period of time;
    forming a first image of the sample based on the detected electrons;
    detecting an abundance of a first plurality ions scattered from a region of the sample, the region of the sample being based on the first image; and
    detecting a second plurality of ions scattered from the sample based on an energy of the second plurality of ions for a second period of time which is greater than the first period of time.

2. The method of claim 1, further comprising forming a second image of the sample based on the detected abundance of the first plurality of ions.

3. The method of claim 2, wherein a region of the sample from which the second plurality of ions is detected is based on the second image.

4. The method of claim 2, wherein the region of the sample from which the second plurality of ions is detected is also based on the first image.

5. The method of claim 2, further comprising forming a third image of the sample based on the energy abundance of the second plurality of ions.

6. The method of claim 5, wherein the first plurality of ions is detected for a third period of time, the third period of time is greater than the first period of time, and the third period of time is less than the first period of time.

7. The method of claim 1, wherein the second plurality of ions is detected after the first plurality of ions.

8. The method of claim 1, wherein the second plurality of ions scattered from the sample is detected based on an angle of the second plurality of ions.

9. The method of claim 1, further comprising forming a second image of the sample based on the energy abundance of the second plurality of ions.

10. The method of claim 1, wherein the second plurality of ions is detected after the first plurality of ions is detected.

11. The method of claim 1, wherein the first plurality of ions is detected after the electrons are detected.

12. The method of claim 1, wherein the first plurality of ions is detected for a third period of time, the third period of time is greater than the first period of time, and the third period of time is less than the first period of time.

13. A method, comprising:
    interacting charged particles with a sample to generate electrons;
    detecting the electrons for a first period of time;
    forming a first image based on the detected electrons;
    after detecting the electrons, detecting an abundance of a first plurality of ions scattered from the sample for a second period of time;
    forming a second image based on the first plurality of scattered ions; and
    after detecting the first plurality of scattered ions, detecting a second plurality of ions scattered from the sample based on energy of the second plurality of ions for a third period of time,
    wherein the second period of time is greater than the first period of time, and the third period of time is greater than the second period of time.

14. The method of claim 13, wherein the charged particles comprise ions.

15. The method of claim 13, wherein the charged particles comprise ions generated by a gas field ion source.

16. The method of claim 13, wherein the charged particles comprise electrons.

17. The method of claim 13, wherein a region of the sample from which the first plurality of ions is detected is based on the first image, and a region of the sample from which the second plurality of ions is detected is based on the second image.

18. The method of claim 17, wherein the region of the sample from which the second plurality of ions is detected is also based on the first image.

19. A method, comprising:
    detecting electrons generated from a sample;
    forming a first image of the sample based on the detected electrons;

detecting an abundance of a first plurality ions scattered from a region of the sample, the region of the sample being based on the first image; and detecting a second plurality of ions scattered from the sample based on an energy of the second plurality of ions, wherein the electrons are detected for a first period of time and the first plurality of ions is detected for a second period of time different from the first period of time, wherein the second plurality of ions is detected for a third period of time, and wherein the second period of time is greater than the first period of time and wherein the third period of time is larger than the second period of time.

20. The method of claim 19, further comprising forming a second image of the sample based on the detected abundance of the first plurality of ions.

21. The method of claim 20, wherein a region of the sample from which the second plurality of ions is detected is based on the second image.

22. The method of claim 20, wherein the region of the sample from which the second plurality of ions is detected is also based on the first image.

23. The method of claim 19, wherein the second plurality of ions is detected after the first plurality of ions.

24. The method of claim 19, wherein the second plurality of ions scattered from the sample is detected based on an angle of the second plurality of ions.

25. A method, comprising:
   detecting electrons generated from a sample for a first period of time;
   forming a first image of the sample based on the detected electrons;
   detecting an abundance of a first plurality ions scattered from a region of the sample for a second period of time which is greater than the first period of time, the region of the sample being based on the first image; and
   detecting a second plurality of ions scattered from the sample based on an energy of the second plurality of ions.

26. The method of claim 25, further comprising forming a second image of the sample based on the detected abundance of the first plurality of ions.

27. The method of claim 26, further comprising forming a third image of the sample based on the detected abundance of the second plurality of ions.

28. The method of claim 25, further comprising forming a third image of the sample based on the detected abundance of the second plurality of ions.

29. The method of claim 25, wherein the second plurality of ions is detected after the first plurality of ions is detected.

* * * * *

UNITED STATES PATENT AND TRADEMARK OFFICE
CERTIFICATE OF CORRECTION

| | | |
|---|---|---|
| PATENT NO. | : 8,669,525 B2 | Page 1 of 1 |
| APPLICATION NO. | : 12/997686 | |
| DATED | : March 11, 2014 | |
| INVENTOR(S) | : Sybren Sijbrandij et al. | |

It is certified that error appears in the above-identified patent and that said Letters Patent is hereby corrected as shown below:

Title Page 2, References Cited Col. 2 (Other Publications), line 3, delete "Beleiving" and insert -- Believing --.

In the Specification

Col. 3, line 23, delete "that" and insert -- than --.

Col. 7, line 38, delete "surface" and insert -- surface. --.

Col. 14, line 48, delete "and or" and insert -- and/or --.

Signed and Sealed this
Tenth Day of June, 2014

Michelle K. Lee
*Deputy Director of the United States Patent and Trademark Office*